United States Patent [19]

Washington

[11] Patent Number: 4,886,508
[45] Date of Patent: Dec. 12, 1989

[54] LADIES EXTERNAL CATHETER ASSEMBLY

[76] Inventor: Douglas L. Washington, 4201 Spring Valley Rd., Ste. 1400, Dallas, Tex. 75244

[21] Appl. No.: 217,456

[22] Filed: Jul. 11, 1988

[51] Int. Cl.[4] .............................................. A61M 1/00
[52] U.S. Cl. .................................... 604/327; 604/347; 604/355
[58] Field of Search ............... 604/327, 328, 329, 330, 604/331, 346, 347, 348, 349, 350, 351, 352, 353, 354, 355-358, 381

[56] References Cited

U.S. PATENT DOCUMENTS

| | | |
|---|---|---|
| 660,388 | 10/1900 | Moberg et al. ...................... 604/354 |
| 2,483,079 | 9/1949 | Williams . |
| 2,571,357 | 12/1950 | Gemora . |
| 2,698,016 | 11/1952 | Andrade . |
| 2,739,595 | 4/1951 | Huggins . |
| 2,842,129 | 7/1958 | Ernstorff . |
| 2,867,215 | 6/1957 | Horton et al. . |
| 2,873,740 | 2/1959 | Wainwright ........................ 604/347 |
| 3,116,734 | 7/1961 | Terman . |
| 3,194,238 | 7/1965 | Breece . |
| 3,349,768 | 10/1967 | Keane .................................. 604/329 |
| 3,424,163 | 1/1969 | Gravdahl ............................. 604/381 |
| 3,528,423 | 9/1970 | Lee ....................................... 604/329 |
| 3,601,125 | 8/1971 | Moss ................................... 604/347 |
| 3,683,914 | 8/1972 | Crowley ............................. 604/329 |
| 3,742,953 | 7/1973 | Lee . |
| 3,906,952 | 9/1975 | Zamist . |
| 3,918,433 | 11/1975 | Fuisz . |
| 4,023,571 | 5/1977 | Comerford et al. . |
| 4,194,508 | 3/1980 | Anderson . |
| 4,198,979 | 4/1980 | Cooney . |
| 4,200,102 | 4/1980 | Duhamel et al. . |
| 4,246,901 | 1/1981 | Michaud et al. . |
| 4,270,539 | 6/1981 | Michaud ............................ 604/347 |
| 4,610,675 | 9/1986 | Triunfol ............................. 604/331 |
| 4,664,663 | 5/1987 | Brier .................................. 604/387 |

FOREIGN PATENT DOCUMENTS 0003537 of 1890 United Kingdom ................ 604/354
2148126 5/1985 United Kingdom ................ 604/347

Primary Examiner—C. Fred Rosenbaum
Assistant Examiner—Mario Costantino
Attorney, Agent, or Firm—Hubbard, Thurman, Turner & Tucker

[57] ABSTRACT

A soft flexible memory retaining ladies catheter assembly having an elongated thin-walled shell enclosing a cavity and a centralized entrance opening in a cover panel, a full flow recessed outlet, an open mesh full flow resilient insert mounted spaced apart below the cover panel extending beyond the entrance opening in supporting contact with the walls of the shell, designed to contain initial spray and splashing with immediate complete flushing to a self-contained leg bag, and a neat panty support for proper placement.

32 Claims, 4 Drawing Sheets

LADIES EXTERNAL CATHETER ASSEMBLY

BACKGROUND OF THE INVENTION

1. Field of the Invention

The present invention relates generally to sanitary protection and more particularly, to sanitary protection for ladies of all ages with various degrees of urinary incontinence. Incontinence may manifest itself as a slow leakage which is more or less continuous, intermittent sporatic discharge or a sudden uncontrollable full flow urination.

The containment or collection of involuntary discharge of fluid waste from an incontinent female is a problem for millions of otherwise healthy women. Although the problem is not unique to women, the differences in anatomy between men and women require that separate devices be made available for the use of each.

In providing a urine collection device for females, reliable functioning, no matter whether the flow is small or large, or the onset is sudden, is of utmost importance. Few things can be more embarassing than a sudden uncontrolled urination which is noticeable by other people. It is highly desirable that any ladies incontinence device be able to handle this possibility without leakage or splashing on clothing or on the floor. Sufficient capacity must be provided consistent with the size of the bladder.

The nature of the condition mandates that many wearers of an incontinence device must keep the device in place against their person for long periods of time. As a result, comfort is very important as is freedom from irritation and chafing which may result from normal movement of the wearer with the device in place. It is also highly desirable to remove the waste fluid from any contact with the body as soon as possible to minimize irritation and infection. Compactness, unobtrusiveness, softness, and flexibility are further highly desirable characteristics which relate to comfort and convenience.

2. Description of the Prior Art

Known urine collection apparatus for females fall into several basic categories. Absorbant garments similar to diapers and sanitary napkins may have a liquid-proof outer layer and inner layers which absorb liquids and hold them until the diaper or napkin is changed. They are bulky, uncomfortable, and generally asthetically offensive as well as psychologically objectionable for most women. They permit prolonged contact of the moist absorbant material with a large area of the body thus giving rise to irritation and even infection of the skin and promote an effective growth medium for bacteria. The contained urine undesirably comes in contact with the vagina for a period of time until such garments or napkins are removed and changed.

Another category of urine collection devices includes cup-like receptacle members which cover the female urethra and are held in close proximity to the body to collect urine and direct it into a drain tube leading to a suitable receptacle or collection bag, either carried on the leg or placed adjacent to the patient if the patient is bedridden. Some of these devices are provided with a vaccuum collecting system to continuously draw off accumulating urine. Many of the devices of this type attempt to avoid leakage by drawing the edges of the cup-like receptacle tight against the uro-genital area to maintain a seal or as much as a seal as possible.

These device have been unsatisfactory for a fully ambulatory person since they are till susceptible to leakage around the edges and create discomfort by interfering with the user's freedom of movement and ability to assume various postures and by limiting the choice of clothing. Special or unusual strap-on systems add to the psychological trauma and are often uncomfortable.

Another category of prior art devices which attempt to deal with the problem of the ambulatory person are seen to be devices that require internal insertion of some part of the device into the vagina in order to help hold the sealing or collecting device in place. Although these devices may function to collect a flow of liquid urine from an incontinent patient, they are necessarily intrusions into the body cavity and are uncomfortable, especially if worn for considerable periods of time. There is also an increased risk of infection, chafing, and irritation caused by the use of internally worn devices. This is especially true since most of the devices of this class are non-disposable.

SUMMARY OF THE INVENTION

The present invention is an entirely externally worn ladies incontinence assembly. The assembly includes an elongated catheter body of thin wall construction enclosing a cavity which contains a removable elongated open mesh screen insert which is in supporting contact with the side walls and bottom of the body. The screen insert is spaced below a cover panel at the top of a body having a centralized opening to accomodate the entrance of fluid. Below the open mesh screen insert in the bottom of the body is a recessed full flow discharge outlet from which a tube leads away from the cavity in the catheter body through a drainage tube to a separate collecting bag which is conveniently strapped to the leg of a wearer. The outlet opening is centrally located under the entrance opening and is a full flow opening.

The catheter body is made of a resiliently deformable molded silicone rubber of the type having a strong "memory" which always returns to its original shape but yet is soft and flexible. It can easily be rolled up or collapsed completely in a person's hands yet it springs back to the original shape when released. The bottom of the body has a generally upward arcuate form longitudinally. Between the front and rear ends and its also transversely arcuate having side walls that meet at the side edges of the upper generally flat cover panel which may also be gently curved longitudinally with the entrance opening slightly lower than the ends.

Because the entrance opening in the cover panel is much smaller than the width of the cover panel whose side edges run generally parallel to each other, the cover panel forms ledges along the upper part of the body where the side walls and the side edges of the cover panel meet. These ledges extend to the edges of the elongated entrance opening centered in the cover panel.

The screen insert is spaced below the entrance opening and generally conforms to the arcuate shape of the body in supporting contact with the body walls and it is also resiliently deformable but much stiffer than the body to prevent collapse of the unit. Each end of the body has a means for fastening attached thereto symmetrically arranged generally in line with the entrance opening. The body is initially crushed easily but offers increasing resistance to further crushing.

The catheter body and screen insert unit is placed in position in the vicinity of the wearer's genital area with the urethra and surrounding tissue partially located in the entrance opening below the level of the upper cover panel. The unit is held in place by a specially designed panty which is fastened to the means for fastening and with the outlet tube extending through the panty downwardly in leak-proof fluid coupling with a collecting bag mounted to the leg or thigh.

The present invention has recognized an important aspect of the way sudden urination occurs in the female due to the fact that the urethra is surrounded by and usually at least partially covered by soft tissue flaps which must be forced away by the pressure of the fluid and which as a result, produces an initial spray before a solid stream is formed. Failure to understand this mechanism has resulted in incontinence devices that do not handle both aspects well. The present invention does.

At the inception of full flow urination, an initial spray of fluid may be directed in almost any direction until a stream is formed. After the stream forms, it is directed downwardly to the outlet through the open mesh screen insert which has substantially no resistance to flow but prevents splashing by breaking the major stream into a plurality of minor streams similar to the action of an aerator faucet. The lips or ledges of the cover panel together with the rest of the body confine the spray within the unit without the necessity of making any kind of hard seal between the catheter body unit and the person of the wearer with the unit in place.

The unit functions with the wearer in a standing, ambulatory, or even in a sitting position and is designed to operate on a full flow basis. The body and the screen insert are impervious to urine, completely non-adsorbent, and hydrophobic for rapid, complete draining. The screen insert retains virtually no liquid and the curved sides and recessed outlet opening permit full and complete draining of the urine from the catheter body. Even the remaining film of liquid quickly beads and collects in drops which run from the catheter body into the collection bag through the tube. Although the unit is especially designed for high volume full flow, it is also effective to collect smaller volume leakages or dripping. Because of rapid and complete drainage, moisture does not remain in contact with sensitive skin.

In view of the foregoing, it is a main object of this invention to provide an entirely external catheter for ladies who are incontinent, in order to provide sanitary protection and to do so by means of an assembly which is unobtrusive and altogether unlike sanitary napkin devices commonly used.

More specifically, it is an object of this invention to provide an externally worn ladies incontinent assembly which operates on a full flow immediate flush principle made of unwettable hydrophobic materials which do not retain moisture.

It is another object of this invention to provide a completely external unit which operates on a full flow-through principle without splashing, and in addition, collects the initial spray of a sudden discharge without leakage.

A further object of this invention is to provide an external catheter assembly which is capable of collecting and holding in a separate bag the entire contents of a sudden discharge of the bladder without splashing or leaking and which permits the sensitive genital tissues to dry because they are not maintained in contact with urine soaked materials.

An additional object of this invention is to provide a completely external ladies catheter which continues to operate effectively to prevent splashing or spray leakage even while it is subject to collapsing or crushing pressures caused by the wearer's body either by itself or in contact with objects, such as a chair, but which immediately returns by memory to its original shape when such forces are removed.

Another object of this invention is an entirely external ladies catheter which is effective to prevent spraying of urine or leakage of urine onto clothing, which can be comfortably worn without the necessity of shaving any pubic hair.

A further object of this invention is to provide a reusable catheter assembly which is constructed of materials which can be cleaned or disinfected.

A further object of this invention is to provide a removable insert which may be replaced if it has been weakened by repeated cycles of crushing and release or to simply avoid the necessity of cleaning or disinfecting after extended periods of use, all without discarding the body itself.

Another object of this invention is to provide an almost normal-looking panty having an elastic waistband and normal appearing leg holes with a vertically oriented elastic band lift running through the crotch and having a complimentary means for fastening to the fastening means on the ends of the body of the catheter to hold it in place snugly and comfortably without unsightly or unusual appearance.

Another object of this invention is to provide an alternative panty support which like the previous object is equipped to snugly hold the catheter body against the genital area but which in addition has the sides of the leg holes cut with overlapping flaps to permit installation of the panty on persons of limited movement while that person is sitting or lying down, without putting the feet through the leg holes.

Those skilled in the art will further appreciate the above-mentioned features and advantages of the present invention as well as other superior aspects thereof upon reading the detailed description which follows in conjunction with the drawings.

DETAILED DESCRIPTION OF THE PREFERRED EMBODIMENT

Figure 1:
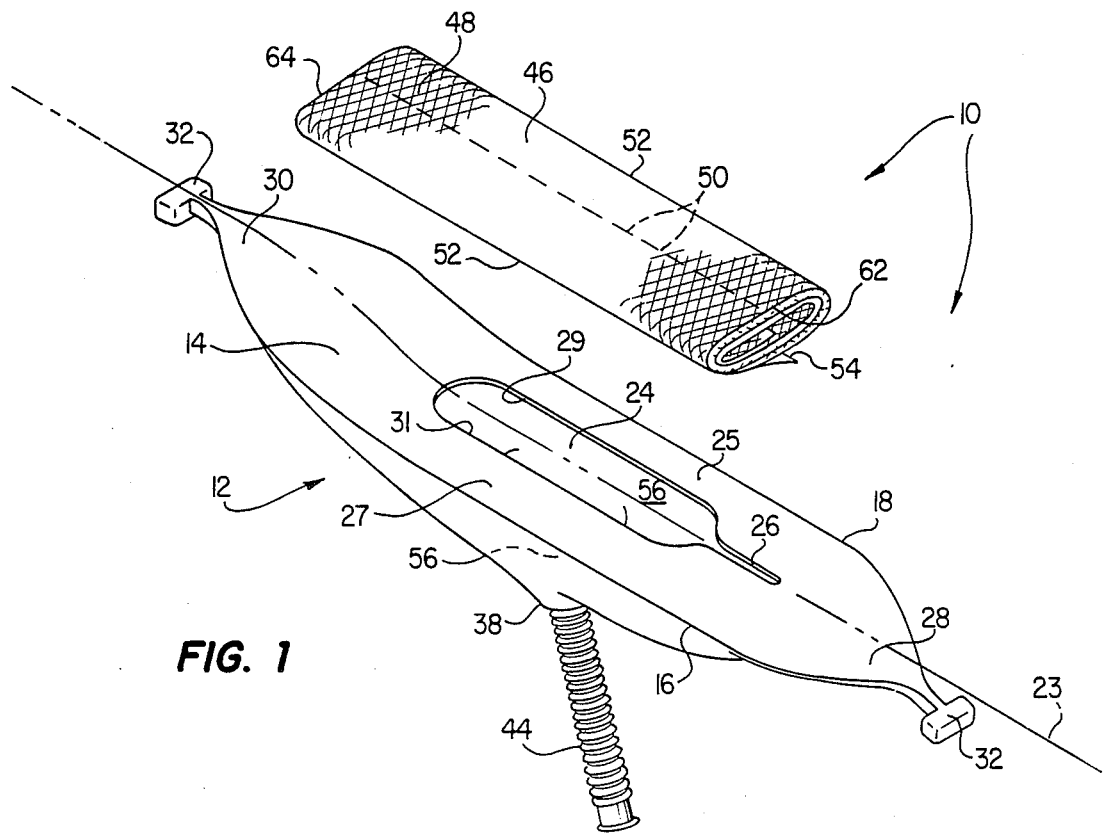
FIG. 1 is a perspective view of the catheter body and a short extension tube connected to the outlet with the elongated open mesh screen insert removed.

In the description which follows, like parts are marked throughout the specification and drawings with the same reference numerals, respectively. The drawings are not necessarily to scale, and certain features of the invention may be exaggerated in scale or shown in schematic or diagramatic form in the interest of clarity and conciseness.

In the FIGS., the catheter, insert, and full flow outlet tube are designated generally by the reference numeral 10. FIGS. 1-4, show a resiliently deformably elongated catheter body 12 having a thin wall enclosing a cavity 56. The upper portion of catheter body 12, the portion which will be placed in contact with a wearer's urogenital tract, has a cover panel 14 best seen in FIG. 1. Cover panel 14 has generally parallel side edges 16 and 18 extending longitudinally along the top of body 12 between a front end 20 and a rear end 22 best seen in FIG. 2. Cover panel 14 has a centrally located elongated entrance opening 24 which is significantly narrower than the width of panel 14 between edges 16 and 18. Ledges 25 and 27 are formed in cover panel 14 between the side edges 18 and 16 and lips 29 and 31 of the entrance opening 24. These ledges are an effective spray and splash guard which confine liquid in the cavity 56

At one end of opening 24 is slot 26 to facilitate insertion of an insert. A front extension 28 and a rear extension 30 are formed as continuations of cover panel 14 beyond ends 20, 22. Extension portions 28, 30 taper at front and rear to terminate in means for fastening 32 at each end generally in line with the entrance opening 24 in panel 14. Means for fastening 32 are oppositely arranged "T" shaped bars with the stem of the "T" generally aligned with the longitudinal axis 23 of the opening 24 and slot 26 and the cross bar of the "T" transversely located as shown. It should be recognized that other means for fastening, such as snaps or clips could be used with corresponding fasteners on the panty means for support to be described.

Figure 2:
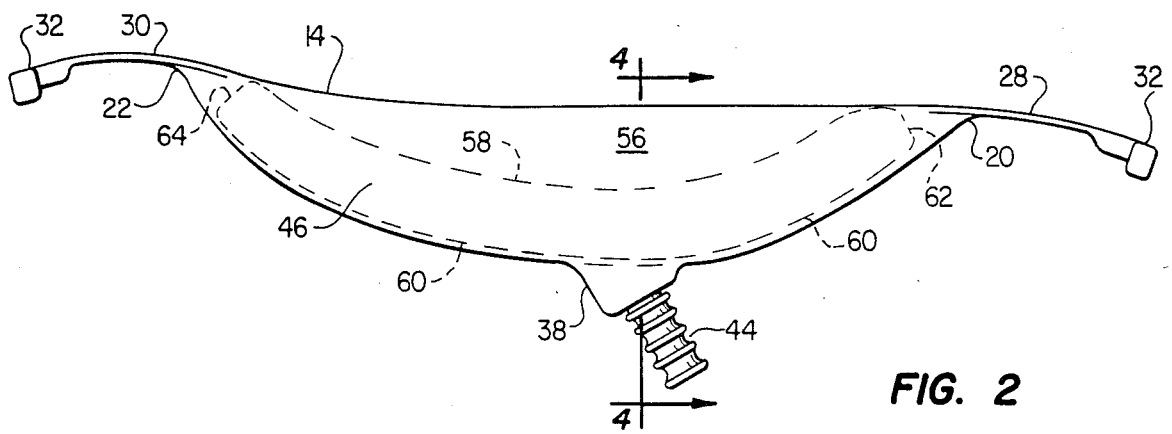
FIG. 2 is a side profile view of the catheter body of FIG. 1 with the open mesh screen insert in place.
Figure 4:
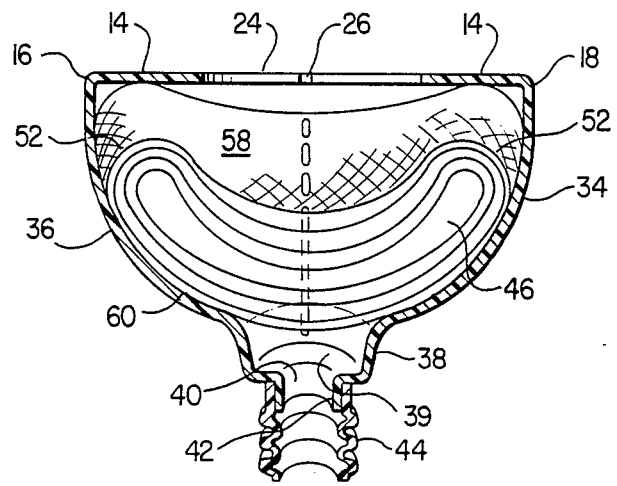
FIG. 4 is a cross-section of the catheter body of FIG. 2 through the outlet opening with an extension tube coupled and containing the open mesh screen insert.

FIG. 4 is a cross-section through the wall of the body as indicated in FIG. 2 which shows the shape of the wall below cover 14. Sidewalls 34 and 36 beginning respectively at side edges 18 and 16 extend downwardly to converge under the cover panel forming the bottom of the body. Side walls 34, 36 are curved arcuately in the transverse direction somewhat in the shape of the cross-section of a boat hull as shown in FIG. 4.

At the lowermost portion of the bottom formed by the side walls, generally centered under entrance opening 24, is a full flow drainage outlet 38 including an opening 40. Drainage outlet 38 is recessed downwardly to form a little cup-like receptacle 39 which aids in collecting any liquid residue to facilitate complete emptying of the catheter body. A short extension of the body wall 42 that forms the opening 40 is used to make a leak-proof coupling with a short full flow discharge tube 44. Tube 44 is designed to be flexible and resilient and to resist collapsing or kinking which would interfere with full flow discharge through the tube. This is illustrated in FIGS. 1-4 in the form of circumferential corrugation-like variations in the diameter of the tube. Outlet 38 is preferably angled toward the front of body 12 for proper positioning when the assembly is worn.

The extreme lowermost portion of the body leading from outlet 38, formed by the wall of the body, is longitudinally tapered upwardly to join the cover panel 14 at the front and at the rear ends of the body. This results in an arcuate shaped body both transversely and longitudinally having its deepest portion where outlet 38 is located. Outlet 38 should be centered directly under entrance opening 24 although both entrance opening 24 and outlet 38 should be located closer to the front end than the rear end, as indicated in FIG. 2.

Catheter assembly 10 includes a removable elongated open mesh screen insert 46 to fit in the catheter body spaced apart below the cover panel. Screen insert 46 permits full flow passage of urine to the discharge outlet without significant resistance to flow. Fluid is completely free to pass through it. It is a separate structure from the body 12 being made from a material that is completely non-absorbent, in the nature of a rolled up screen having unequiaxed diamond-shaped openings 48. Multiple layers of the screen material are wrapped to create an oval shape with a definite depth dimension. Insert 46 is held together by urine impervious stitching 50 running longitudinally along its length as illustrated in FIG. 1. The longitudinal stitching may create a slight longitudinally extending depression along the top and bottom of the insert by pulling the surfaces closer together.

The sides 52 are rounded and generally parallel to each other. The free end 54 is at the bottom of insert 46 and when placed in body 12 will be down against the wall of the body so as to avoid any possible irritation in case parts of the soft tissue of the wearer should come in contact with the insert through the entrance opening as for example when a wearer is sitting.

The longest points of diamonds 48 point towards sides 52 in a transverse direction and the shortest points of diamonds 48 are oriented longitudinally pointing towards the front and rear of the insert. This, together with the elongated shape and the wrapping of the screen material, makes the insert easier to bend longitudinally along its length than transversely across its width. It has more resistance to crushing forces directed against the sides. That feature creates the same property in the body when the insert is used with the cathether body. Although the body has "memory" and will return to its original shape after deforming forces are removed, it is still rather soft and flexible and needs the insert to provide "spongy" resistance to crushing.

Figure 3:
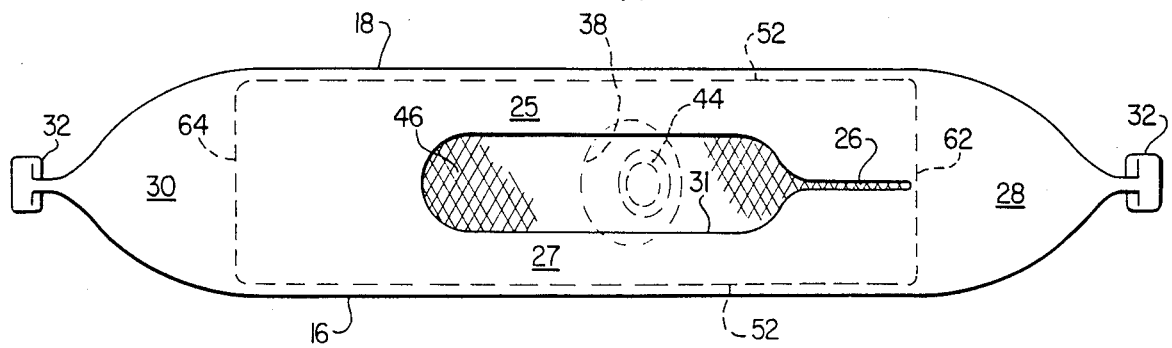
FIG. 3 is a plan view looking down on the catheter body shown in FIG. 2.

The insert 46 fits inside cavity 56 of body 12, as seen in FIG. 2, bent longitudinally in a concave shape lying along the tapered bottom of body 12. It has an upper surface 58 and a lower surface 60 with a front end 62 and a rear end 64 with its top surface 58 spaced apart below opening 24. It occupies a substantial portion of the cavity in the body and extends towards the ends of the body beyond the ends of opening 24 as illustrated in FIG. 3.

FIG. 4 shows that insert 46 is also bent transversely in a convex shape with its bottom surface 60 in supporting contact with the wall of the bottom of the body. In the central area of the body, the screen insert is of lesser thickness than the body depth to leave a space between the opening in the cover panel and the upper surface of the insert when in place.

Figure 5:
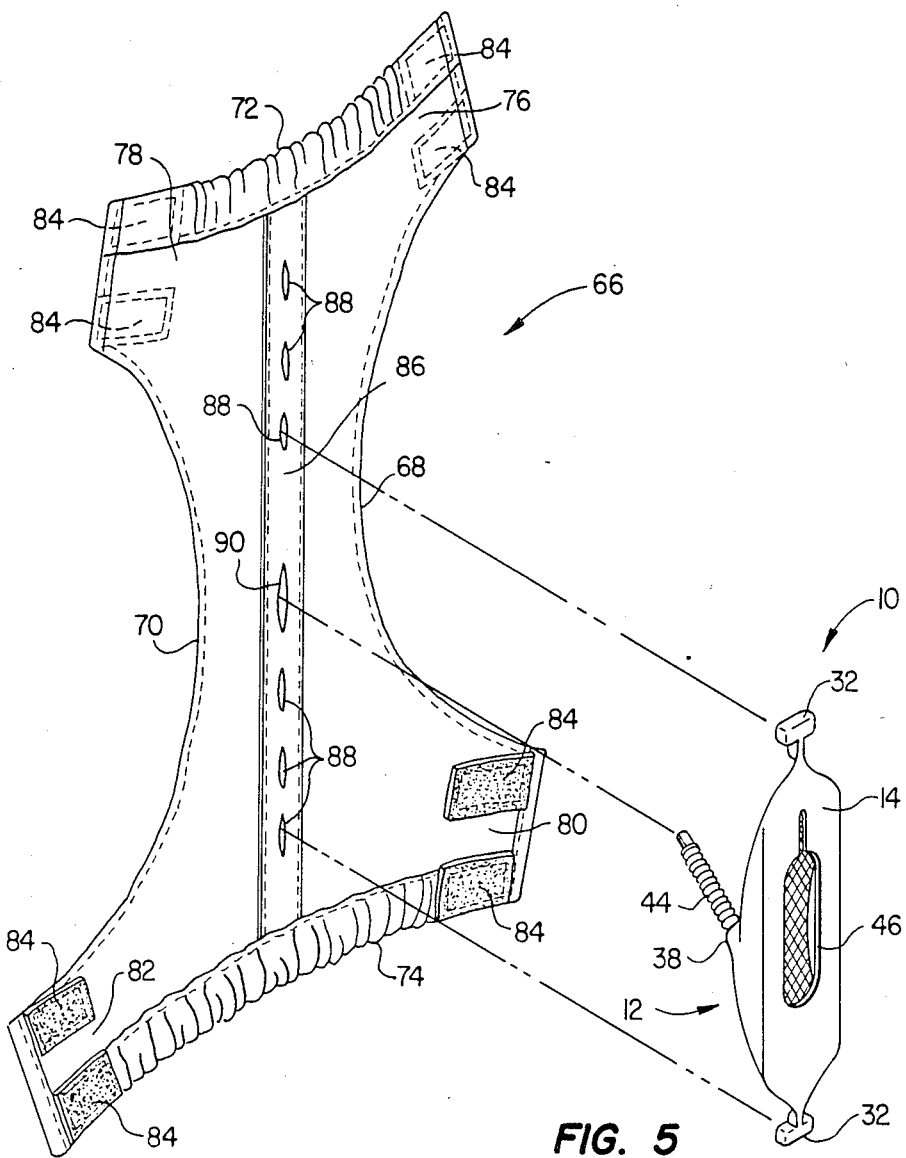
FIG. 5 is an exploded view of the catheter shown in FIGS. 1-3 as used with the specialized panty shown in FIGS. 6 and 7.
Figure 6:
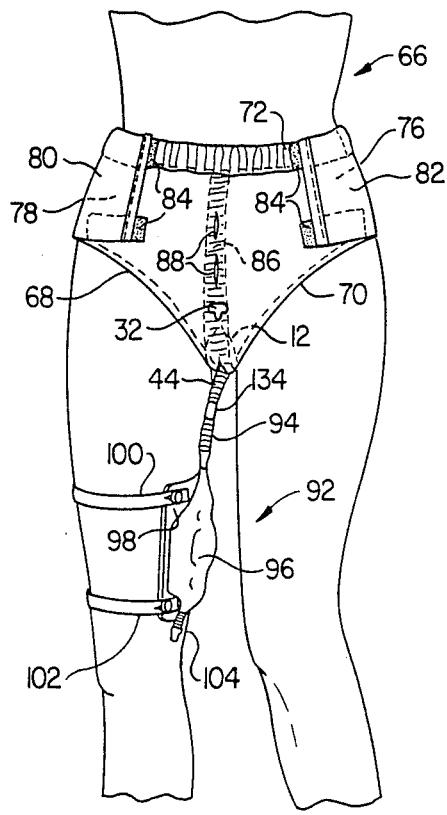
FIG. 6 is a front view of the specialized panty of FIG. 5 in place on a wearer with the catheter body connected to a collection bag mounted for use on the wearer's leg.
Figure 7:
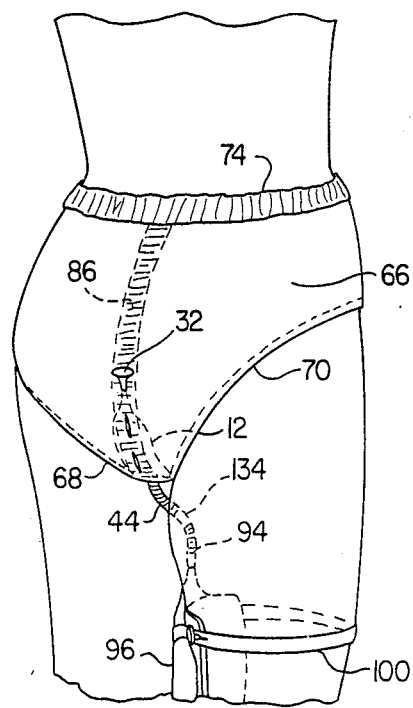
FIG. 7 is a rear view of the specialized panty assembly of FIG. 6.

Referring now to FIG. 5, is a means for supporting the catheter assembly 10 in position for use. A modified panty-like garment designated generally by the reference numeral 66, is shown in exploded view laid out in the flat. Modified panty 66 is made from a piece of fabric, most suitably fabric made from man-made fiber which is soft but not absorbent. It is cut for leg openings 68 and 70 having a crotch between and includes front waistband 72 and rear waistband 74 which will be located respectively at the front and rear of a wearer's waist as shown in FIGS. 6 and 7 when modified panty 66 is worn. The waistbands are elastic for a comfortable fit.

Adjacent front band 72 are side flaps 76 and 78 at opposite ends of front waistband 72 and side flaps 80 and 82 adjacent band 74 located at opposite ends of waistband 74. Each of side flaps 76, 78, 80, and 82 has one or more VELCRO ™ pads 84 which are spaced and located to cooperate with each other to hold the garment in place. As is indicated in FIG. 6, side flaps 80, 82 overlap side flaps 76, 78, respectively and are secured by the VELCRO ™ pads 84 which are located on opposite sides of the fabric as indicated in FIG. 4. Pads 84 for side flaps 76, 78 are on one side of panty 66 and pads 84 on side flaps 80, 82 are one the opposite side of the fabric. The combination of the elastic waistband and some permissible alteration in the placement of the flaps allows adjustment for comfort and to accomodate some variation in the waist of the wearer.

Centered through the crotch area and running generally perpendicular to and extending between waistbands 72, 74 is an elasticized lift band 86 having a series of spaced apart buttonhole-like openings 88 which constitute a means for supporting means for fastening means 32 on either end of catheter body assembly 10 by connection therewith. As is indicated in FIG. 5, one of the support means 32 is turned and placed through an opening 88 and the other means for support 32 is turned and placed through a spaced apart other opening 88 in lift 86 while tube 44 is placed through a centralized tube opening 90 spaced apart from, and in line with the other buttonhole-like openings 88.

This puts the tube on the outside of the modified panty as indicated in FIG. 6 for connection to a collector bag. Lift 86 being an elasticized band tends to help hold the upper surface 14 of the cover panel against the crotch area of the wearer and allows for some give in response to ordinary movement of the wearer. FIG. 7 shows the wearer of FIG. 6 with the device in place seen from the rear.

FIG. 6 also illustrates the urine collecting leg bag assembly generally designated by the numeral 92 including a means for fastening the bag to a wearer's leg or thigh and a removably coupled full flow inlet tube removably coupled to the discharge outlet. Full flow inlet tube 94 is coupled in leak-proof liquid communication with short tube 44 and urine collecting bag 96. These tubes may be removably coupled together via connector 134. Bag 96 is mounted on a panel 98 which rests against the leg. Panel 98 is preferably made from a soft flexible fabric-like material to which is fastened upper strap 100 and lower strap 102 by conventional means, said straps being conventionally adjustable whereby the urine collecting leg bag can be preferably attached above the knee to a leg of the wearer and can be conveniently detached for emptying when desired, without removing the panty 66 or the catheter assembly 10. Bag 96 is preferably equipped with drain faucet 104 which facilitates emptying or running clean water through the bag for cleaning as desired.

It is easily seen that full flow connecting tubes 44, 94 have the properties of softness, flexibility, and resistance to collapse which make it possible for the wearer to be completely ambulatory without difficulty. Resistance to kinking serves to prevent interruption of full flow from catheter body 12. Full flow is meant to be the ability to accomodate on a continuous basis the full stream of fluid generated by a wearer during uncontrolled urination without filling body 12 with liquid. These tubes and the openings associated therewith preferably have a diameter of about $\frac{1}{4}$ to $\frac{1}{2}$ inch.

Figure 8:
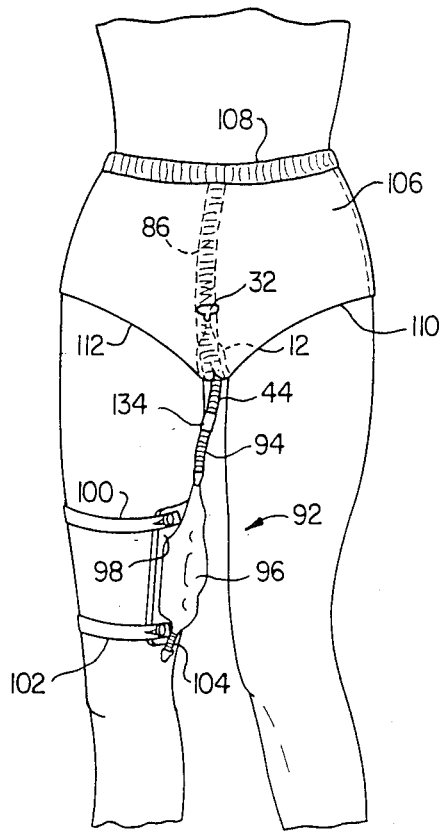
FIG. 8 shows a wearer using a regular panty adapted to hold the catheter body in proper position in fluid connection with a collection bag fastened to the wearer's leg.
Figure 9:
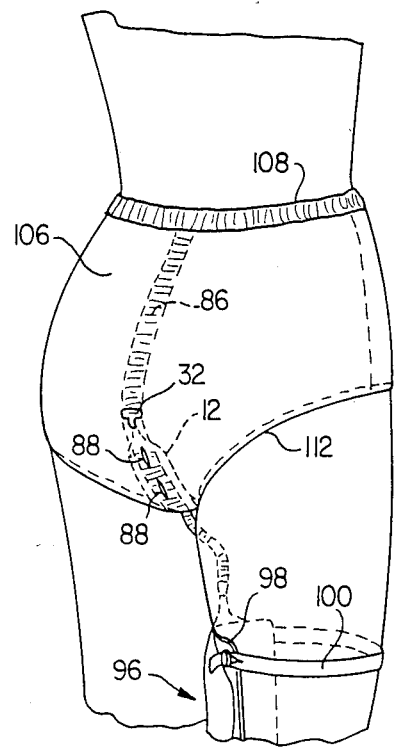
FIG. 9 is a rear view of the completed assembly shown in FIG. 8.

The modified panty 66 has an additional benefit for some wearers over the more nearly conventional panty shown in FIGS. 8 and 9, because modified panty 66 can be placed on the body without placing the feet and legs through leg holes. This is an advantage with respect to persons who have a limited range of movement or for placement on a person who has difficulty standing or is confined to a wheelchair. Because the sides are cut and it opens up, the panty can be placed on the person who is reclining or sitting.

For the person with the normal range of movement, panty 106 in FIG. 8 and 9 has a regular type elasticized waistband 108 all around conventional leg openings 110 and 112 with the same lift 86 running generally in a vertical direction through the crotch perpendicular to waistband 108 and connected thereto at front and rear. It is connected the same way to the means for fastening 32 of catheter assembly 10 and utilizes the same leg bag assembly 92, except that it does not have the cut sides and flaps as does panty 66. In fact, panty 106 is exactly like a conventional panty except for the lift 86 running through the crotch having spaced apart buttonhole-like slits to support the catheter unit and provide an opening for the full flow drainage tube.

Figure 10:
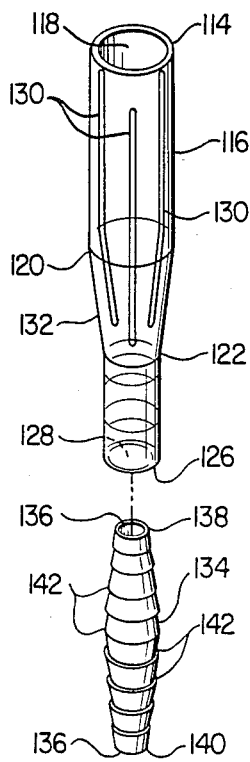
FIG. 10 is an exploded perspective view of an alternative discharge tube and tube connection which may be used instead of the discharge tube shown in FIGS. 1-4.

In FIG. 10 alternate discharge tube 114 is preferably molded from the same silicone rubber material as is body 12. Discharge tube 114 has a straight wall portion 116 having an opening 118. At transition 120 the wall of tube 114 tapers inwardly to a smaller diameter at transition 122 where it has another straight portion 124 terminating at outlet 126 having opening 128. A series of spaced apart ribs 130 on the inside of tube 114 extending along straight portion 116 and tapered portion 132 add to the resistance to crushing or kinking and improve the strong memory characteristic of tube 114.

Connector 134 has an elongated barrel shape with a full flow opening 136 throughout its length. It is adapted to have its end 138 inserted in opening 128 of discharge tube 114 wherein straight portion 124 is expanded by the insertion and holds it by friction. It may include a series of circumferential rings 142 which vary in diameter to a maximum at the middle and which facilitates insertion and holding of the connector. Opposite end 140 is similarly adapted to be inserted in a inlet tube 94 (FIGS. 6–8) leading to a leg bag 92. Connector 134 may be used in a similar fashion with discharge tube 44.

Figure 11:
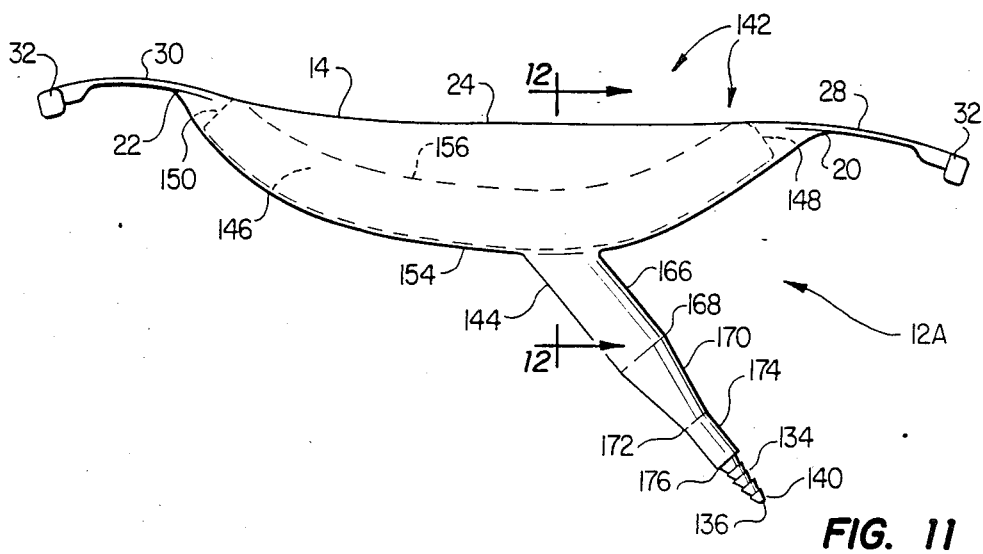
FIG. 11 is a side view of a modified catheter assembly with a molded in discharge outlet tube, connection and an alternative continuous void sponge structure insert.

In FIG. 11 is a side view showing a modified catheter assembly designated generally by the reference numeral 142. It has a body 12A which is exactly like body 12 everywhere except at the discharge outlet and discharge tube 144 at the lower most and slightly forward portion of the body 12A. That constitutes a molded in discharge tube 144 to be further described. Body 12A has cover panel 14, front end 20, rear end 22, front extension 28, rear extension 30 and a means for fastening 32 at each end. Inside body 12A shown in dotted outline is an alternate insert 146 having a continuous void sponge structure. Catheter assembly 142 includes the body 12A with the molded in discharge outlet tube 144 and the removable elongated alternate insert 146, said insert having a front end 148, a rear end 150, a bottom surface 154, and a top surface 156. Alternate insert 146 like insert 46 has a primary purpose to resist compression and collapse of the body 12A and at the same time allow unobstructed fluid passage through it. Insert 146 facilitates full flow passage of urine to the discharge outlet without significant resistance to flow and without splashing. It is made of completely non-absorbent hydrophobic material in the nature of a lattice work of interconnected hexagonal shaped fibers containing a very high percentage of void space.

Figure 12:
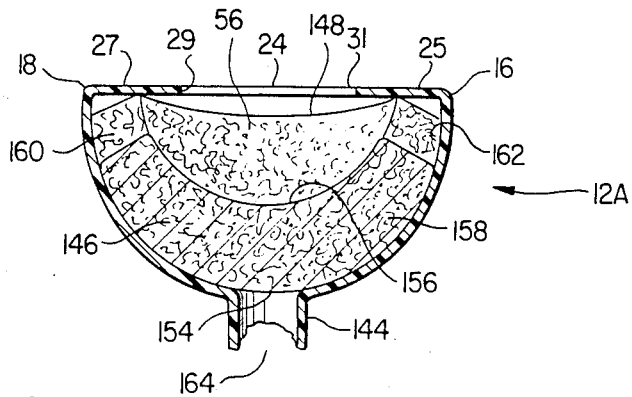
FIG. 12 is a cross-section through the catheter body and alternative continuous void sponge structure insert of FIG. 11 with molded in discharge outlet opening.

In FIG. 12 the interconnected fibers are indicated as 158. Also as indicated in FIG. 12, the sides 160, 162 of insert 146 may be squared off such that insert 146 essentially has a rectangular shape when laid out flat. The sides 160 and 162 then would be generally parallel to each other and perpendicular to ends 148, 150. As is indicated in FIG. 11 when inserted into body 12A the bottom 154 of insert 146 lies in supporting contact along the arcuate surface of the bottom wall of body 12A and as indicated in FIG. 12 is also in supporting contact with the side walls of body 12A, arcuate in the transverse direction as well. The more severe compression caused by the greater curvature in the transverse direction causes the body 12A with insert 146 to have a greater resistance to deformation in the transverse direction, as by a squashing action between the legs, than it does to bending in the longitudinal direction defined by the front and rear of the device. This insert also provides "spongy" resistance to crushing. Insert 146 fits inside cavity 56 of body 12A in a similar manner to that of screen insert 46 of FIGS. 2 and 3. It lies bent longitudinally in a concave shape lying along the tapered wall of body 12A. It occupies a substantial portion of the cavity in the body and extends toward the ends of the body beyond the ends of opening 24 in body 12A, just like insert 46 does. It is bent transversely in a convex shape with its bottom surface 154 in supporting contact with the wall of the bottom of body 12A. In the central area of the body, the screen insert is a lesser thickness than the body depth to leave a space between opening 24 of cover panel 14 and the upper surface 156 of insert 146 when in place. This space allows part of the uretha and surrounding soft tissue to extend below the opening in cover panel 14 without continuous contact with the insert that could result in uncomfortable chafing.

Molded in discharge tube 144 is a continuation of the wall of body 12A having an opening 164 constituting an outlet from body 12A through which fluid can pass completely unobstructed with full flow through insert 146, and by its location at the bottom most portion of body 12A facilitates complete drainage from the adjoining arcuate sloping sides of body 12A. Molded in discharge outlet tube 144 has, like discharge outlet tube 114, a straight portion 166 leading to a transition 168, a tapered reduced diameter portion 170 another transition 172 having a final straight portion 174 terminating in an outlet opening 176. Elongated barrel shaped connector 134, as in FIG. 10, has lower end 140 and full flow opening 13 therethrough for complete drainage of any fluid entering body 12A through opening 24. Opening 164 is preferably located directly beneath and centered below opening 24 in body 12A. This aids free flow removal of fluid forcefully ejected downward directly into the drainage outlet, the fluid stream being broken up into a plurality of smaller streams by the insert without significant resistance to flow.

Connector 134 is adapted to be removably connected both to the end of discharge outlet tube 144 and to a tube 94 leading to a leg bag assembly 92. A friction fit is preferred so that the wearer can remove the inlet tube 94 for the purpose of emptying bag 96 without removing body 12A from her person. Discharge outlet 144 fits through and extends out of the supporting panty of FIGS. 6–9 just like discharge outlet tube 44 shown therein.

In the best mode, the catheter body is molded from silicone rubber in one piece with a continuous wall which has a strong "memory" characteristic, but which is otherwise quite soft and flexible to the extent that it can be deformed and crushed or even rolled up by a person's hands, but which immediately springs back to its original molded shape when deforming forces are removed. The silicone rubber used is impervious to liquid, although it is actually somewhat porous to passage of gas through the walls which is a desirable characteristic because a limited amount of "breathing" can occur.

The outlet tube 144 is preferably molded in as discharge outlet tube 144, a permanent part of the body which is formed from the same material. Alternately, it may be a separate tube coupled to outlet 38 as is shown in FIG. 4 and as such, can be made of the same or different material. Applicant believes that the silicone rubber material and suitable molding techniques are known in the rubber molding industry although it is a developing art. An "anti-twist" molding technique is preferable largely for asthetic appearance so that the catheter body is uniform in shape even after repeated deformations in use.

A material that has been satisfactory is supplied by Dow Corning Corporation of Midland, Michigan U.S.A., which is called Dow Corning Liquid Silicone Rubber No. 595. Dow Corning also has subsidiaries in Blacktown, New South Wales, Mississauga Ontario, Brussels Belgium, and in Mexico and Japan. A similar injection molding grade silicone rubber material is believed to be available from General Electric Company. The silicone rubber has a nice soft feel for the wearer, is smooth and has no sharp edges which could create discomfort or irritation. The basic body 12, 12A itself is easily deformable in the fingers of one hand.

Dow Corning sells the silicone rubber under the brand name Silastic LSR which when injection molded 30 seconds at 200 degrees C. (392 degrees F.) is said to have the following typical properties.

| | |
|---|---|
| Durometer, Shore A | 40 |
| Tensile Strength, MPa (psi) | 8.5 (1225) |
| Elongation, percent | 500 |
| Tear Strength, Die B, kN/m (ppi) | 35 (200) |

| | -continued | |
|---|---|---|
| Modulus @ 100% MPa (psi) | | 1.0 (150) |
| Resilience, Bashore | | 50 |
| Compression Set, 22 hrs @ 175° C. (348° F.), percent (ASTM D 395 Method B) | | 50 |

This data comes from page 12 of a Dow Corning published product information brochure entitled "Silastic LSR, A Guide to Product Performance", which is incorporated herein by reference.

A Dow Corning sales specification for SILASTIC 595 liquid silicone rubber parts (A) and (B) dated May 17, 1984 lists the minimum value for the preferred SILASTIC 595 material when tested under the following conditions:

For the following tests, mix 50 parts of SILASTIC 595 Part A with 50 parts of SILASTIC 595 Part B, deair, and press cure a 0.075 (0.191 cm) inch thick test slab 5 minutes at 150 C.

| Specific Gravity | 1.08-1.15 | CTM 0022 | ASTM D 792 Method A1 |
|---|---|---|---|
| Durometer, Shore A2 | 38-48 | CTM 0099 | ASTM D 2240 |
| Tensile Strength, psi | 850 minimum | CTM 0137A | ASTM D 412 Die C |
| Elongation, % | 350 minimum | CTM 0137A | ASTM D 412 Die C |
| Tear, Die B, ppi | 150 minimum | CTM 0159A | ASTM D 624 |

The tests identified as "CTM" are Dow Corning test methods which are said to be available on request. "ASTM" is the American Society for Testing Materials, a trade institution. Applicant wishes to emphasize that this information is set forth in compliance with its duty of disclosure as representing material that has been selected as being suitable for the construction of Applicant's catheter device as having excellent feel which provides comfort and the important memory characteristic which allows the catheter body to immediately spring back to its original shape after deformation when released. Applicant has not performed any of these tests and merely reports what the supplier has provided in the way of test specifications for material that has satisfactory characteristics in Applicant's invention. Applicant has relied upon the supplier to help select the specific material to be used by the injection molder to produce the desired shape and characteristics of the invention according to the inventor's general specification The opening in the cover panel must be large enough to accomodate in part, the lowermost portion of the urethra and soft tissue surrounding the urethra and is preferably an elongated opening that will accomodate some misalignment in the front to rear direction and accomodate some slight variation in the size of the respective tissues and parts in normal variations among women.

Some idea of appropriate size of the catheter body is as follows as a general guide. The overall length is about 10 inches (25 cm), overall width between the outside edges 16, 18 of the cover panel is about 2 ¼ inches (5.7 cm) and length where the arcuate bottom rises up to meet the cover panel between 20, 22 is about 6 ½ inches (16.5 cm). Centralized depth of the body at the deepest point is about 1 ¼ inches (3.2 cm) tapering to about 1 inch (2.5 cm) halfway to the points 20, 22. The top opening 24 is about 1 inch (2.5 cm) wide and 3 ¼ inch (8.3 cm) long with about a 1 inch (2.5 cm) narrow slot 26 at one end for ease in inserting or removing an insert. The body walls are preferably thicker than the top panel and may be of increasing thickness toward the bottom and where the outlet is located, according to good molding technique. The cover panel is preferably slightly over 1/32 inch thick (0.0079 cm) with the adjoining body wall about slightly over 1/16 inch thick (0.16 cm). Around the lip 29, 31 of the entrance opening 24 is a thickened rounded bead about twice as thick as the cover panel proper, which serves to help with the rising up action of the edges of the opening when the catheter body is subject to deforming forces and which strengthens the edge of the opening all around.

The screen from which the open mesh screen insert is made is preferably polypropylene or a similar plastic material which is non-absorbent, not affected by urine, and is hydrophobic. While being deformable, the material must resist compression and collapse. The diamond-shaped openings of insert 46 are approximately a ¼ inch long between the farthest points and approximately ⅛ inch wide between the closest points of the diamond. The solid portions between the diamonds are slender, almost like heavy monofilament fishing line, and are joined to each other where they cross. Three layers on top and bottom have been found satisfactory. The amount of open or void area in the open mesh screen insert (and between the wraps) is vastly greater than the volume occupied by the crossing lines.

An alternative material for insert 146 is known in the plastic art which is a three dimensional structure made of interconnected hexagonal ring-like fiber which is also believed to be useful for making an insert because it is deformable yet resists crushing. It returns to its original shape and does not offer any significant resistance to the passage of a stream of liquid because of the great amount of open void space separated by only narrow interlocking solid connections. Any of the suitable screen inserts will literally pass the full flow of an ordinary water faucet without splashing back in the vertical direction and the alternate material referred to will do so also.

In operation, the screen or alternate insert is placed in the body in the manner illustrated in FIGS. 2 or 11 and is curved in both directions as is indicated in FIGS. 2 and 4 or 10 and 11. The outlet opening and tubing is selected to more than accomodate the maximum flow of a full uncontrolled urination. The object is to get the liquid right through to the collection bag on a real time basis without any accumulation of liquid in the catheter body itself while at the same time the body, and especially the ledges adjacent the opening in the cover, confine and control any limited initial spray or splashing. It is undesirable for liquid to be held or retained in the any part of the catheter body which is designed to drain quickly and completely.

It is recognized that because the catheter body is placed between the legs and, although elongated, it still occupies some width and is subject to some pressure from the legs of the wearer. However, pressure on the sides of the device with an insert in place, causes the lips 29, 31 of ledges 25, 27 to rise up in response to such pressure. This tends to provide a fail-safe mode of operation because deforming pressures tend to make it more effective rather than less effective.

The assembly is not rigid and will deform under pressure of the wearer's body, but the additional stiffness provided by the insert assures that total collapse will not occur under any but the most extreme conditions, even with the wearer sitting on the device. The assembly requires no additional equipment such as a vacuum pump and does not include disposable components. It may be reused over and over without ill effect. It is simple and compact. It is attractive compared to other devices of this type, especially in regard to the supporting structure which is virtually indistinguishable from normal undergarments. There is less of the stigma associated with the incontinent condition and the assembly is more comfortable to wear, less irritating, and economical to make.

Although preferred embodiments of the present invention have been described in detail here, those skilled in the art will recognize that various substitutions and modifications can be made to the specific embodiments disclosed without departing from the scope and spirit of the invention as described in the appended claims.

What is claimed is:

1. A ladies external catheter assembly comprising:
   a resiliently deformable elongated catheter body having a thin wall enclosing a cavity, said wall including a cover panel with a centrally located elongated entrance opening between front and rear ends of the body, said opening being large enough to accept the urethra and surrounding tissue when said panel is placed in contact with a wearer's person, the body further having a full flow discharge outlet in the wall of the body, spaced below the cover panel, and
   a removable elongated open mesh screen insert to fit in the catheter body spaced apart below the cover panel, the screen insert being resiliently deformable along with the body in response to user forces and tending to return the body to its original shape by supporting contact with the walls of the body, said screen insert having such open mesh construction which permits full flow passage of urine to the discharge outlet without significant resistance to flow.

2. The ladies catheter assembly of claim 1 wherein the assembly further includes a urine collecting bag having means for fastening the bag to a wearer's leg or thigh, said bag having a removably coupled full flow inlet tube removably coupled to the discharge outlet.

3. The ladies catheter of claim 2 wherein the body further includes an extension at both ends generally in line with the entrance opening, each end extension terminating in means for fastening the catheter body to a support.

4. The ladies catheter assembly of claim 3 further including a means for supporting the catheter body on a wearer through connection with the means for fastening located at each end of the body, to hold the catheter body in place against the wearer's body with the urethra and surrounding tissue located below the opening in the cover panel, extending part way into the catheter body, to permit passage and collection of urine without splashing.

5. The ladies catheter assembly of claim 4 wherein the means for supporting the catheter in position of use is a panty-like garment having a conventional waistband with openings for a wearer's legs separated by a crotch area through which an elasticzed band passes having a series of spaced apart buttonhole-like openings for fixing the means for fastening of the catheter body to hold the catheter in proper position, at least one of said holes being located to allow the short exit tube leading from the outlet to pass through for connection to the collection bag when the assembly is worn.

6. The ladies catheter assembly of claim 5 further including openable flaps with fastening means at the sides of the garment which can be separated for easy placement or removal of the garment in catheter supporting position on a wearer without the necessity of stepping through the leg holes.

7. The ladies catheter assembly of claim 6 wherein the resiliently deformable catheter body has a memory characteristic and soft, flexible feel provided by silicone rubber construction.

8. The ladies catheter assembly of claim 2 wherein the full flow discharge outlet has a cup-like recessed are surrounding the outlet.

9. The catheter of claim 1 wherein the discharge outlet at the bottom of the catheter body includes a short extending tube in fluid communication with the discharge outlet to allow full flow drainage from the catheter body through the tube.

10. The ladies catheter of claim 9 wherein the body further includes an extension at both ends generally in line with the entrance opening, each end extension terminating in means for fastening the catheter body to a support.

11. The ladies catheter assembly of claim 10 further including a urine collecting bag having a means for fastening the bag to a wearer's leg or thigh, said bag having a full flow inlet tube removably coupled to the short tube extending from the outlet of the body.

12. The ladies catheter assembly of claim 11 further including a means for supporting the catheter body on a wearer through connection with the means for fastening located at each end of the body, to hold the catheter body in place against the wearer's body with the urethra and surrounding tissue located below the opening in the cover panel, extending part way into the catheter body, to permit passage and collection of urine without splashing.

13. The ladies catheter assembly of claim 12 wherein the means for supporting the catheter in position of use is a panty-like garment having a conventional waistband with openings for a wearer's legs separated by a crotch area through which an elasticized band passes having a series of spaced apart buttonhole-like openings for fixing the means for fastening of the catheter body to hold the catheter in proper position, at least one of said holes being located to allow the short exit tube leading from the outlet to pass through for connection to the collection bag when the assembly is worn.

14. The ladies catheter assembly of claim 13 further including openable flaps with fastening means at the sides of the garment which can be separated for easy placement or removal of the garment in catheter supporting position on a wearer without the necessity of stepping through the leg holes.

15. The ladies catheter assembly of claim 14 wherein the resiliently deformable catheter body has a memory characteristic and soft, flexible feel provided by silicone rubber construction.

16. A ladies external catheter assembly comprising:
   a resiliently deformable liquid tight body having a thin wall enclosing a cavity, said body having an upper cover panel with generally parallel side edges extending between a front end and a rear end with side walls beginning at the side edges of the cover and extending downwardly to converge under the cover forming the bottom of the body, said bottom tapering upwardly to meet the cover at said ends, said cover having a generally centrally located opening for the female urethra and surrounding tissue, said bottom directly below the opening in the cover, having a full flow discharge outlet connection with opening suitable to drain fluid from all parts of the cavity, and an elongated resiliently deformable removable full flow-through open mesh insert to fit in and occupy a substantial portion of the cavity in the body, said insert extending toward the ends of the body beyond the opening in the cover panel, with one side of the insert in contact with the bottom of the body in supporting contact with its wall, said insert being of lesser thickness than the body depth to leave a space between the opening in the cover panel and the upper surface of the insert when in place.

17. The catheter of claim 16 wherein the discharge outlet at the bottom of the catheter body includes a short extending tube in fluid communication with the discharge outlet to allow full flow drainage from the catheter body through the tube.

18. The ladies catheter of claim 17 wherein the body further includes an extension at both ends generally in line with the entrance opening, each end extension terminating in means for fastening the catheter body to a support.

19. The ladies catheter assembly of claim 18 further including a urine collecting bag having a means for fastening the bag to a wearer's leg or thigh, said bag having a full flow inlet tube removably coupled to the short tube extending from the outlet of the body.

20. The ladies catheter assembly of claim 19 further including a means for supporting the catheter body on a wearer through connection with the means for fastening located at each end of the body, to hold the catheter body in place against the wearer's body with the urethra and surrounding tissue located below the opening in the cover panel, extending part way into the catheter body, to permit passage and collection of urine without splashing.

21. The ladies catheter assembly of claim 20 wherein the means for supporting the catheter in position of use is a panty-like garment having a conventional waistband with openings for a wearer's legs separated by a crotch area through which an elasticized band passes having a series of spaced apart buttonhole-like openings for fixing the means for fastening of the catheter body to hold the catheter in proper position, at least one of said holes being located to allow the short exit tube leading from the outlet to pass through for connection to the collection bag when the assembly is worn.

22. The ladies catheter assembly of claim 21 further including openable flaps with fastening means at the sides of the garment which can be separated for easy placement or removal of the garment in catheter supporting position on a wearer without the necessity of stepping through the leg holes.

23. The ladies catheter assembly of claim 22 wherein the resiliently deformable catheter body has a memory characteristic and soft, flexible feel provided by silicone rubber construction.

24. The ladies catheter assembly of claim 17 wherein the full flow discharge outlet has a cup-like recessed area surrounding the outlet.

25. The ladies catheter assembly of claim 24 wherein the resiliently deformable catheter body has a memory characteristic and soft, flexible feel provided by silicone rubber construction 26. The ladies catheter assembly of claim 16 wherein the assembly further includes a urine collecting bag having means for fastening the bag to a wearer's leg or thigh, said bag having a removably coupled full flow inlet tube removably coupled in fluid communication to the discharge outlet.

27. The ladies catheter of claim 26 wherein the body further includes an extension at both ends generally in line with the entrance opening, each end extension terminating in means for fastening the catheter body to a support.

28. The ladies catheter assembly of claim 27 further including a means for supporting the catheter body on a wearer through connection with the means for fastening located at each end of the body, to hold the catheter body in place against the wearer's body with the urethra and surrounding tissue located below the opening in the cover panel, extending part way into the catheter body, to permit passage and collection of urine without splashing.

29. The ladies catheter assembly of claim 28 wherein the means for supporting the catheter in position of use is a panty-like garment having a conventional waistband with openings for a wearer's legs separated by a crotch area through which an elasticized band passes having a series of spaced apart buttonhole-like openings for fixing the means for fastening of the catheter body to hold the catheter in proper position, at least one of said holes being located to allow the short exit tube leading from the outlet to pass through for connection to the collection bag when the assembly is worn.

30. The ladies catheter assembly of claim 29 further including openable flaps with fastening means at the sides of the garment which can be separated for easy placement or removal of the garment in catheter supporting position on a wearer without the necessity of stepping through the leg holes.

31. The ladies catheter assembly of claims 30 wherein the resiliently deformable catheter body has a memory characteristic and soft, flexible feel provided by silicone rubber construction.

32. The ladies catheter assembly of claim 16 wherein the resiliently deformable catheter body has a memory characteristic and soft, flexible feel provided by silicone rubber construction.

* * * * *